United States Patent [19]

Berber et al.

[11] 4,226,532
[45] Oct. 7, 1980

[54] DEVICE FOR GRANULOMETRIC ANALYSIS OF PARTICLES IN FLUIDS

[76] Inventors: Viktor A. Berber, ulitsa Shelkovichnaya, 184, kv. 65; Evgeny S. Pervushin, ulitsa Shelkovichnaya, 182, kv. 71; Khafiz M. Murtazin, ploschad Degtyarnaya, 6 Internatsionalny proezd, 20; Vladimir G. Kholin, ulitsa Shelkovichnaya, 184, kv. 53, all of Saratov, U.S.S.R.

[21] Appl. No.: 924,100

[22] Filed: Jul. 12, 1978

[51] Int. Cl.³ .............................................. G01N 15/02
[52] U.S. Cl. .................................... 356/336; 250/574; 356/339
[58] Field of Search ............... 356/336, 339, 341, 243; 250/564, 565, 574

[56] References Cited

U.S. PATENT DOCUMENTS

| | | | |
|---|---|---|---|
| 3,493,304 | 2/1970 | Rovner | 356/339 |
| 4,110,043 | 8/1978 | Eisert | 356/336 |

Primary Examiner—John K. Corbin
Assistant Examiner—Matthew W. Koren
Attorney, Agent, or Firm—Fleit & Jacobson

[57] ABSTRACT

According to the invention, the device for granulometric analysis of particles contained in fluids comprises a feeding channel and a receiving channel intended for passage of a fluid under investigation. The two channels communicate with each other through a nozzle. The ratio between the diameters of the nozzle and the receiving channel is in the range of ¼ to 1/7. The receiving channel is provided with transparent windows for passage of a light flux emitted by a lighting means through the fluid in that channel. The device further includes a light-sensitive means to receive light reflected from particles contained in the fluid.

4 Claims, 2 Drawing Figures

DEVICE FOR GRANULOMETRIC ANALYSIS OF PARTICLES IN FLUIDS

FIELD OF THE INVENTION

The present invention relates to measuring instruments and, more particularly, to devices for granulometric analysis of particles in fluids, i.e. to devices intended to determine the quantity and size of extraneous particles contained in fluids. The invention is chiefly applicable to the analysis of suspensions of low concentrations, such as the analysis of impurities contained in fuels and lubricants.

BACKGROUND OF THE INVENTION

There is known a spectrometer for granulometric analysis of particles contained in gases. The spectrometer comprises a chamber through which there is directed a flow of a particle-containing gas, such as air (aerosol), and a light source which emits a beam of light to traverse the aerosol flow. To maintain the laminarity of the aerosol flow at the point of its intersection with the light beam, the aerosol flow is confined in a flow of filtered air.

There is known an optical sensor for determining the quantity of particles in a sample of a fluid. The sensor comprises a flow-through cell with two windows. Passed through the cell is a liquid envelope into which a fluid sample is introduced. The liquid envelope separates the sample from particles on the cell walls and directs, with great accuracy, particles of the sample to the focus of the light beam arriving through the windows provided in the cell.

There is further known a device for granulometric analysis of particles contained in fluids.

The device comprises a feeding channel for the supply of fluid to be analyzed. The feeding channel communicates through a tubular nozzle with a receiving channel which is of a great diameter and arranged coaxially with the feeding channel. Spaced in the annular gap between the tubular nozzle and the walls of the receiving channel are pipes for the supply of pure liquid to form a liquid envelope encompassing the flow of the fluid being investigated. The receiving channel is provided with transparent windows to admit a light flux into the fluid flowing through the channel. The light flux is emitted by a lighting means whose optical axis extends at an angle to the axis of the nozzle.

The device under review further includes a light-sensitive means to receive light reflected from particles contained in the fluid being investigated. The light-sensitive means is arranged so that its optical axis passes through the point of intersection of the axis of the nozzle and the optical axis of the lighting means.

The optical properties of the liquid envelope must be identical with those of the fluid under investigation. Such an identity can best be achieved when the fluid being analyzed and the liquid envelope are of the same composition, but the fluid used to form the liquid envelope is pure, i.e. rid from all foreign particles with sizes in excess of the sensitivity threshold of the light-sensitive means.

The above requirement makes it imperative that the device should include such components as a fluid tank, a pump and a high-performance fluid purifying unit.

In addition, provision must be made for a special means to equalize the velocities of the fluid being investigated and the liquid envelope in order to prevent their mixing at the point where the flow of liquid being investigated is traversed by the light beam, i.e. prevent a transfer of particles from the fluid being analyzed to the liquid envelope.

There is another important consideration: a device of the foregoing type is normally used to analyze different fluids, which necessitates a change of the liquid envelope, keeping in mind that the optical properties of the latter must be identical with those of the fluid subjected to analysis. However, such changes effect the overall rate of analysis and increase the costs involved.

SUMMARY OF THE INVENTION

It is the principal object of the present invention to improve the efficiency of the device for granulometric analysis of particles contained in fluids.

Another object of the invention is to ensure a high accuracy of granulometric analysis of particles contained in fluids, while using simplified equipment for the analysis.

Still another object of the invention is to cut down the costs involved in the granulometric analysis of particles contained in fluids.

The foregoing objects are attained by providing a device for granulometric analysis of particles contained in fluids, comprising a feeding channel which communicates through a nozzle with a receiving channel provided with transparent windows for passage of a light flux emitted by a lighting means through the fluid under investigation flowing in that channel, the optical axis of the lighting means extending at an angle to the axis of the nozzle, the device further including a light-sensitive means to receive, through a separate window, light reflected from particles contained in the fluid being analyzed, the optical axis of the light-sensitive means passing through the point of intersection of the axis of the nozzle and the optical axis of the lighting means, which device is characterized, according to the invention, in that the ratio between the diameters of the nozzle and the receiving channel is in the range of $\frac{1}{4}$ to 1/7.

In order to reduce the noise current in this device which does require a liquid envelope around the flow of fluid being analyzed, it is expedient that the feeding and receiving channels should be arranged at a perpendicular to each other to match the optical axis of the light-sensitive means with the axis of the nozzle; it is also expedient that the window transparent to the reflected light should be provided in the wall of the feeding channel opposite to the outlet of the nozzle.

In order to reduce the contamination of the device with foreign particles, it is advisable that the feeding and receiving channels and the internal surfaces of the nozzle should be inclined downward in the downstream direction.

In order to remove gas bubbles from the fluid being investigated, the receiving channel can be arranged vertically with its inlet being at a lower level than its outlet.

The device according to the invention for granulometric analysis of particles contained in fluids makes it possible to investigate both individual samples of fluids and constant flows of fluids without providing a liquid envelope around the fluid under investigation. This feature, in turn, makes it possible to considerably simplify the design of the device and accounts for a high accuracy and efficiency of the analysis.

BRIEF DESCRIPTION OF THE ATTACHED DRAWINGS

Other objects and advantages of the present invention will become more apparent from the following detailed description of preferred embodiments thereof, taken in conjunction with the accompanying drawings, wherein.

DETAILED DESCRIPTION OF THE INVENTION

Figures 1, 2:
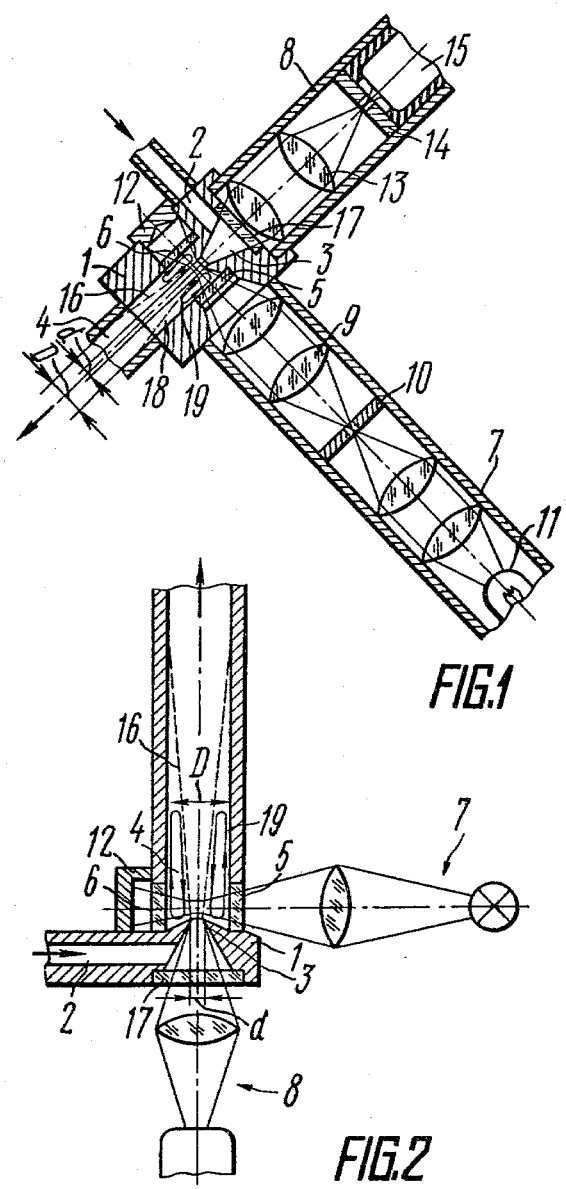
FIG. 1 is a diagram of a device for granulometric analysis of particles in fluids with inclined channels, in accordance with the invention.
FIG. 2 is a diagram of a device for granulometric analysis of particles contained in fluids with a vertical receiving channel, in accordance with the invention.

According to FIG. 1, the device for granulometric analysis of particles contained in fluids comprises a chamber 1 provided with a feeding channel 2 which communicates through a cone-shaped nozzle 3 with a receiving channel 4 having transparent windows 5 and 6.

The channel 4 extends coaxially with the nozzle 3 and at a perpendicular to the channel 2. The windows 5 and 6 serve to pass a light flux emitted by a lighting means 7 through the liquid being investigated, which flows in the channel 4. The optical axis of the lighting means 7 is arranged at a right angle to the axis of the nozzle 3. Mounted on the chamber 1 is a light-sensitive means 8. The latter is arranged so that its optical axis passes through the point of intersection of the axis of the nozzle 3 and the optical axis of the lighting means 7. The lighting means 7 comprises a set of lenses 9, a diaphragm 10 and a light source 11. Light passing through the receiving channel 4 is absorbed by a light trap 12. The light-sensitive means 8 comprises lenses 13, a diaphragm 14 and a light-sensitive element 15 which is a photoelectron multiplier. The nozzle 3 serves to form a flow 16 (shown by the dash line) of the fluid to be investigated. The ratio between the diameters d and D of the nozzle 3 and the receiving channel, respectively, is in the range of ¼ to 1/7.

The feeding channel 2 and the receiving channel 4 extend at a right angle to each other. The nozzle 3 is arranged at the inlet of the receiving channel 4. The optical axis of the light-sensitive means 8 is matched with the axis of the nozzle 3. Provided in the wall of the feeding channel 2, opposite to the outlet of the nozzle 3, is a window 17 which is transparent to the light flux reflected from particles contained in the fluid under investigation and received by the light-sensitive means 8.

The feeding channel 2, the receiving channel 4 and the internal surfaces of the nozzle 3 are slanted downward in the direction of the flow of the fluid being investigated.

The taper of the nozzle 3 must be as small as possible because of hydraulic losses, although it must not be less than the spatial angle defined by the collimating ray of the light-sensitive means 8.

The embodiment of FIG. 2 differs from that of FIG. 1 in that the receiving channel 4 is vertical, in that the inlet of the receiving channel 4 is at a lower level than the outlet, and in that the nozzle 3 is at the lower portion of the channel 4.

The device according to the invention for granulometric analysis of particles contained in fluids operates as follows.

The fluid to be analyzed is pumped through the feeding channel 2 (FIG. 1) and the nozzle 3 to the receiving channel 4, wherein the flow 16 of that fluid is produced. In a volume 18 of the fluid being investigated, around the submerged flow 16, there are produced circular whirls 19 (shown by the arrows). The whirls 19 are produced by the forces of friction (viscosity) caused by the interaction between the flow 16 and the fluid in the volume 18. Between the volume 18 and the flow 16 there is an exchange of fluid that mainly occurs in that portion of the receiving channel 4 which is remote from the nozzle 3 and close to the place where the divergent flow 16 reaches the wall of the receiving channel 4. The volume 18 is limited; this factor and the above-mentioned exchange of fluid account for a rapid removal of bubbles from the volume 18.

At this point where the light beam emitted by the lighting means 7 intersects the flow 16, the diameter of this light beam must be somewhat greater than that of the flow 16 to prevent the passage of particles outside the lighted zone. Suspended particles of impurities contained in the fluid being investigated travel across the zone illuminated by the light beam whose focus is in immediate proximity to the outlet of the nozzle 3. As foreign particles do so, they produce a pulse of reflected light. Some part of the light energy reflected by a particle, whose amount is determined by the solid angle formed by the tapered shape of the nozzle 3, is transmitted through the window 17, the lenses 13 and the diaphragm 14 to the cathode of the photoelectron multiplier which produces a corresponding current pulse to be applied to a secondary instrument, such as an indicator (not shown).

Selecting the ratio between the diameters of the nozzle 3 and the receiving channel 4 in the range of ¼ to 1/7 makes it possible to perform granulometric analysis without providing a liquid envelope. This factor, in turn, accounts for a simpler design of the device and an increased rate of investigation. The foregoing ratio is selected because of a number of reasons.

A decrease in the diameter D of the receiving channel 4, while the diameter d of the nozzle 3 remains unchanged, produces the following effects:

(a) an increase in the sensitivity of the device due to a smaller thickness of the layer of fluid exposed to light;

(b) better conditions for the removal of bubbles, due to a decrease in the volume 18.

On the other hand, due to a decrease in the diameter D of the receiving channel 4, the transparent windows 5 and 6 are brought closer together, as well as closer to the nozzle 3 and the light-sensitive means 8. As a result, the light scattered by the surface of the windows 5 and 6 may raise the level of noise currents and thus affect the sensitivity of the device. The above-mentioned ratio between the diameters d and D of the nozzle 3 and the receiving channel 4, respectively, is established experimentally in compliance with all the foregoing conditions.

The fact that the channels 2 and 4 and the internal surfaces of the nozzle 3 are inclined downward in the downstream direction is conducive to a faster removal of particles precipitated from the fluid being investigated. This prevents contamination of the channels 2 and 4 which otherwise may affect the accuracy of analysis. In this case the window 17 is above the flow of fluid, which rules out a precipitation of particles on the surface of that window 17 and a loss of sensitivity.

Precipitation of particles largely occurs when the pumping is discontinued. It is necessary to stop the pumping at regular intervals when investigating individual samples of fluids or a flow of fluid containing bubbles, for example, air bubbles. If this be the case, an analysis must be preceded by a removal of bubbles from the sample, because otherwise the bubbles may be sensed as particles.

The embodiment of FIG. 2 is preferable for investigating continuously pumped fluids without bubbles. The embodiment of FIG. 2 operates as that of FIG. 1. The former differs from the latter by a faster removal of the air contained in the channels 2 and 4 and the nozzle 3 prior to the arrival of the fluid to be investigated. This is due to the fact that the vector of the buoyancy force essentially coincides with the direction of the flow.

What is claimed is:

1. A device for granulometric analysis of particles contained in fluids, comprising: a feeding channel having an inlet and an outlet; a nozzle arranged at said outlet of said feeding channel; a receiving channel having an inlet and an outlet; its inlet communicating through said nozzle with said outlet of said feeding channel; said feeding and receiving channels being intended to contain a fluid pumped therethrough; said receiving channel having aligned windows formed therein for exposing the fluid to a light flux and arranged on opposite sides of the channel; a lighting means whose optical axis is spaced from and extends at an angle to the axis of said windows, said windows being positioned in a portion of said receiving channel closely spaced from said nozzle so that the optical axis passes through fluid flowing in a diverging flow path; a third window formed in one of said channels, intended to receive light reflected from particles contained in the fluid in the diverging flow path; a light-sensitive means whose optical axis extends through the point of intersection of the axis of said nozzle and the optical axis of said lighting means, said light-sensitive means being arranged opposite to said third window; the ratio between the diameters of an outlet of said nozzle and said receiving channel being in the range of $\frac{1}{4}$ to 1/7.

2. A device as claimed in claim 1, wherein said feeding and receiving channels extend at a perpendicular to each other, said optical axis of said light-sensitive means passing through the axis of said nozzle, and said third window being provided in a wall of said feeding channel, opposite to the outlet of said nozzle.

3. A device as claimed in claim 2, wherein said feeding and receiving channels and internal surfaces of said nozzle are inclined downward in the downstream direction.

4. A device as claimed in claim 2, wherein said receiving channel is vertical, its inlet being at a lower level than its outlet.

* * * * *